United States Patent [19]

Hussmann

[11] Patent Number: 4,994,272
[45] Date of Patent: Feb. 19, 1991

[54] PROCESS AND APPARATUS FOR FREEING BITTER LUPIN SEED OF BITTER SUBSTANCES THEREIN

[75] Inventor: Peter Hussmann, Florence, Italy

[73] Assignee: Inter-Mittex AG, Switzerland

[21] Appl. No.: 403,012

[22] Filed: Jul. 12, 1989

Related U.S. Application Data

[63] Continuation of Ser. No. 840,050, Mar. 17, 1986, abandoned, which is a continuation-in-part of Ser. No. 482,335, Apr. 4, 1983, Pat. No. 4,576,820.

[30] Foreign Application Priority Data

May 21, 1982 [DE] Fed. Rep. of Germany ....... 3219245

[51] Int. Cl.$^5$ .................... A01W 65/00; A01N 17/08
[52] U.S. Cl. .................................. 424/195.1; 424/79
[58] Field of Search .......................... 424/195.1; 71/79

[56] References Cited

FOREIGN PATENT DOCUMENTS 0329201 11/1920 Fed. Rep. of Germany .

OTHER PUBLICATIONS

Chem. Abst. 16(9) 594 1922.
Lango, *Boll. Soc. Ital. Biol.*, "Action of the Aqueous Extract of Lupinus Albus, on the Movements of the Isolated Uterous of the Rabbit and Guinea Pig", vol. 24, 1179-81 (1948).
Rewald, *Chimiker-Zeitung*, "The Removal of Bitterness From Lupines", vol. 45 (No. 131), pp. 1053-1064 (Nov. 1, 1921).
Chem. Abst. 43:8532c, 1949.
Chem. Abst. 94:63991k, 1981.
Chem. Abst. 89:195713c, 1978.
Chem. Abst. 75: 115949g and: 115950a, 1971.

*Primary Examiner*—John W. Rollins
*Attorney, Agent, or Firm*—Foley & Lardner, Schwartz, Jeffery, Schwaab, Mack, Blumenthal & Evans

[57] ABSTRACT

A process for treating bitter lupin seeds, wherein the seed is reduced to a very fine particle size either before or during a countercurrent extraction using aqueous solutions which contain differing concentrations of lupin-seed extract, produces a material containing bitter substances extracted from the lupin seed which can be used as a biologically active agent, for example, to affect the growth of plants.

18 Claims, 3 Drawing Sheets

PROCESS AND APPARATUS FOR FREEING BITTER LUPIN SEED OF BITTER SUBSTANCES THEREIN

This application is a continuation of U.S. patent application Ser. No. 840,050 filed Mar. 17, 1986, abandoned which is a continuation-in-part of U.S. patent application Ser. No. 482,335 filed Apr. 4, 1983, U.S. Pat. No. 4,576,820.

BACKGROUND OF THE INVENTION

The present invention relates to a processed apparatus for debittering bitter lupin seed, and to the use of material derived from bitter lupin seed as a biologically active agent.

The bitter lupin is a crop plant that was grown in ancient Egypt and later all over the Mediterranean region and in South America. Due to a high content (40% and over) of completely digestible protein and an oil content of 15% to 20% in its seed, the bitter lupin is valued as a nutrient for man and animals.

But before bitter lupin seed may be used as a food for man or animals, it has to be freed of its bitter substances. This is necessary not only to eliminate a bitter taste but also to assure that the bitter substances are not the cause of the so-called lupin disease, which is particularly a problem in the case of domestic animals.

In one well-known process for freeing lupin seed of bitter substances, the lupin seed is first -boiled and then steeped in water for up to 48 hours. The drawbacks of this process are that it is complex and expensive, and that there is a marked loss in the food value of the lupin seed. Furthermore, large amounts of water are needed for the process, and there is the problem of contamination to surface and subsurface waters into which the waste may run. There are also debittering processes that employ solvents other than water, but such processes have serious shortcomings.

In addition to the use of bitter lupin seed as a food for man and a feedstuff for animals, the seed has been used in a milled form as a material for promoting the growth of plants. The effects of milled lupin seed on the growth of plants are small, however.

SUMMARY OF THE INVENTION

Another object of the present invention is to provide a debittering process for lupin seed which can be carried out with only a small expenditure of energy, while at the same time retaining most of the nutritive value of the lupin seed and allowing the recovery of bitter substances for further use.

Another object of the present invention is to provide a composition comprising a product of the aforesaid process which can be used as a biologically active agent.

Yet another object of the present invention is to provide a method for treating plants with material derived from bitter lupin seed so as to affect the growth of the plants.

In accomplishing the foregoing objects, there has been provided, in accordance with one aspect of the present invention, a method for extracting bitter substances from lupin seed, wherein the seed is reduced to a very fine particle size either before or during counter-current extraction, while cold, against aqueous lupin-extarct solutions of differing strengths. More specifically, a process has been provided for treating particulate material comprised of bitter lupin seep, which material contains extractable bitter substances, comprising the steps of (a) providing a series of separate extract solutions, each solution of said series having a differing concentration of said bitter substances, said series having at least a highest-, a second highest-, and a lowest-concentration extract solution; (b) providing a filter medium comprised of a layer of the particulate material, which filter medium is contacted by the highest-concentration extract solution in the series; (c) sequentially contacting the layer with each extract solution of the remaining extract solutions in the series, respectively, in a predetermined order of decreasing concentration of bitter substances; (d) after step (c), contacting the layer with pure water; (e) removing the highest-concentration extract solution from the series, so that the second highest-concentration extract becomes the highest-concentration extract solution in the series; and (f) repeating steps (b) through (e) at least once, wherein (i) the particulate material is comprised of bitter lupin seed which is reduced to a particle size in the range of about 1 to 50 microns, (ii) the layer of the particulate material is between about 5 and about 50 mm in thickness, (iii) the highest-concentration extract solution contains a percentage of dry mass between about 10 and 30%, and (iv) steps (b), (c) and (d) are carried out at a temperature of about 30° C. or less.

In accordance with another aspect of the present invention, there has been provided a composition that comprises a material containing bitter substances extractable from bitter lupin seed, the material being a product of the above-described process. In a preferred embodiment, the composition further comprises a physiologically compatible carrier, such as water, in which the bitter substance-containing material is soluble.

In accordance with yet another aspect of the present invention, a method has been provided for treating plants, comprising the step of applying to a plant an amount, sufficient to affect the growth of the plant, of a composition containing bitter substances extracted from bitter lupin seed .

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art.

DETAILED DESCRIPTION OF THE PREFERRED EMBODIMENTS

One advantage of the process of the present invention is that, while only water is used as a solvent without the input of heat, a debittering extraction operation is effected which does not result in significant decline in the protein content of the lupin seed material and, moreover, keeps any loss of nutrients which does occur within specific limits. Also, such loss is limited to the so-called nitrogen-free extracts.

In the process of the present invention, the alkaloids present in the lupin seed are recovered in a concentrated form, together with substances occurring with them, and so can be put to some use. Accordingly, the small loss in nutrient value can be readily balanced economically In fact, the nutrient loss is generally outweighed by the fact that the concentrates of the extracts, in either a liquid or dry form, are highly effective materials for promoting plant growth, as described in greater detail below. Furthermore, the concentrates can be used as insecticides and herbicides, and for pharmacological purposes.

The apparatus for carrying out the process of the present invention comprises a milling unit and at least one extraction unit with a filtering lower plate or stage for taking up the lupin seed to be debittered, and with sequentially connected storage spaces for taking up the lupin seed extract solutions.

An advantage of the apparatus described above is that it is designed for industrial use and can, when run continuously, produce large amounts of debittered lupin seed for food and animal feed purposes At the same time, large amounts of very valuable lupin extract, containing the bitter substances, is produced which be put to many different uses, particularly in agriculture and forestry.

Further details and advantages of the present invention will be apparent from the detailed account given below of the process of the present invention and of the apparatus for use in connection therewith.

Figure 1:
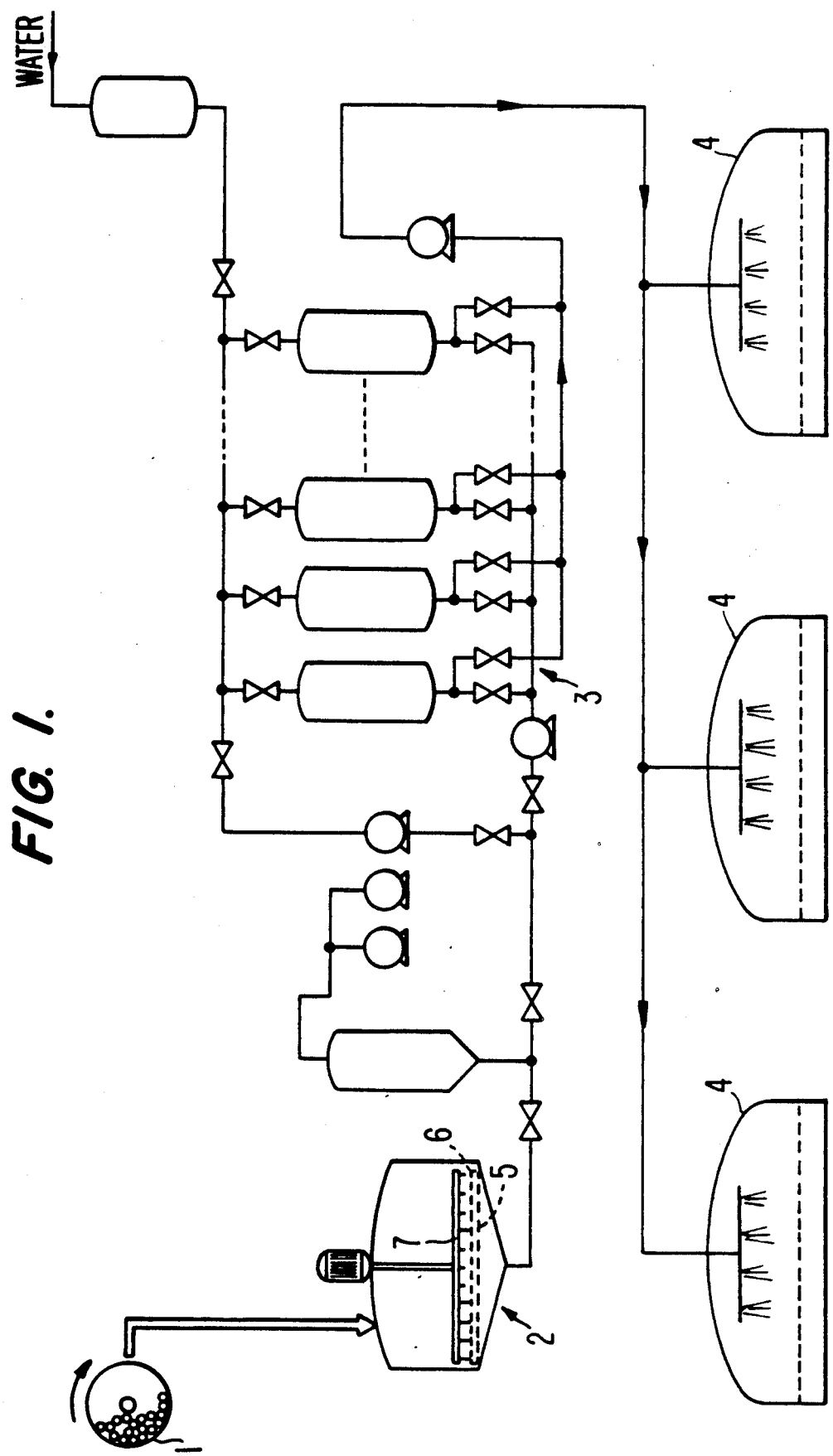
FIG. 1 is a schematic drawing of apparatus adapted to carrying out an extraction process within the present invention.

With reference to FIG. 1, the main parts of the apparatus for effecting an extraction process in accordance with the present invention are a ball mill 1, a flat bed filter extractor 2, and a number of storage vessels 3 connected with each other in circuit and with extractor 2. In addition to these basic elements, the apparatus has parts well known to those trained in the relevant art, such as valves, pumps, separators and storage units, for which no further account is given. Another component of apparatus for carrying out the extraction process of the present invention is a drying apparatus having a number of drying housings 4, which is used for drying the lupin-seed extract of alkaloids and substances occurring therewith. Extractor 2 has a lower filter plate or stage which is made up of a grating 5 and a piece of filter fabric 6 provided thereon, filter 6 is preferably made of very fine mesh material. The filter fabric is most preferably a monofilament fabric of synthetic resin such as polypropylene, a polyester or polyamide. The filter is provided on the lower plate of the extractor so that separation of the extraction solutions after contact thereby with the very finely milled solids can be undertaken by vacuum.

Extractor 2 also has an agitator 7 which is part of a system that may be moved up and down. The extractor further comprises an apparatus for smoothing over the filter cake formed on the stage of the filter. The same apparatus can be used for lifting the filter cake clear of the lower stage of the filter and for cleaning the filter fabric Another form of mill can be used in place of a ball mill, although a ball mill is preferred because of its very good milling properties The lupin seed can be milled to a very fine particle size, in the range of 1 to 50 microns, before being subjected to the countercurrent extraction. Alternatively, the lupin seed can be reduced to the 1-to-50 micron size range by first coarsely milling the seed and, thereafter, agitating (e.g., by vigorously stirring) the filter medium comprised of the milled seed during the extraction to achieve the desired particle size.

In place of a single extractor, a number of extractors can be joined together by piping and, in some cases it is possible to dispense with the bank of vessels, if the extract solutions can be stored in the extractors themselves and in the piping which joining them together The time of storing the separate amounts of solution is cut down by increasing the number of extractors.

An account will now be given of an extraction process in keeping with the present invention. A certain amount of unhulled lupin seed to be extracted is mixed with water, or with a lupin extract solution comprised of water and extracted materials containing bitter substances, as produced in an earlier process stage, in a ratio between about 1:4 to 1:10, particularly about 1:5 to 1:6. The resulting mixture is run into ball mill 1, in which the materials are milled for 2 to 12 hours, or for a shorter time. The effect of the milling is that the lupin seed (which can be broken down somewhat beforehand) can be milled thereafter without any dust, so that the ground lupin seed has a size in a range of 1 micron to 50 microns. The cellulose of the seed, which is broken down because of this very fine milling, is very important if one is optimize the high nutritional value of the debittered lupin seed.

After milling, the lupin seed is extracted in extractor 2. The milled seed, converted to a slurry by the wet milling operation, is placed on the stage of the filter in extractor 2 as a layer having a height of about 5 to 50 mm, preferably 10 to 25 mm. The milled lupin seed is then washed in countercurrent fashion with amounts of extract solution produced beforehand from water and extracted materials containing lupin-seed bitter substances. The milled lupin seed is thereafter washed with pure water, preferably distilled water.

A more detailed account of the extraction process will now be given. The lupin seed extract solutions stored in storage vessels 3 are mixed in the order of decreasing concentration, separately and one after the other, with the particulate starting material comprised of milled lupin seed and lupin extract solution. The operation is started with the extract solution having the highest concentration of bitter substances, and ends with the extract solution having the lowest concentration. After the extract solutions are removed from contact with the starting material, pure solvent, preferably water, is mixed with the starting material, which is more or less completely spent, and then run off as a weak solution In this process, the concentration of every solution goes up to a value equal to the value of the solution supplied in the immediately preceding step before mixing with the starting material. The solutions, each becoming more concentrated in the extractor, are run back (after going through the extractor) into that storage container in which a solution with the concentration in question had before been stored. The solution with the highest concentration produced after extracting a given amount of milled lupin seed is run off into drying housings 4 for drying, and its place is taken by fresh solvent. The spent mass of starting material is taken from extractor 2 and replaced by newly milled lupin seed. A further extraction takes place along the above-described lines. All stages of the extraction process are undertaken without the supply of heat.

To produce the lupin extract solutions having differing concentrations of bitter substances, water is mixed initially with a new batch of very finely milled lupin seed. A solution is thereby produced which is pumped off from the starting material, again with a gradual decrease in the concentration of bitter substances extractable therefrom. This solution, becoming lower and lower in its concentration, undergoes division into a number of amounts of different concentration, and is stored in vessels 3. The spent mass of starting material is then replaced by a new batch of very finely milled lupin seed, and the amounts of solution are mixed, one after the other, with the fresh starting material. The concentration of each extract solution is thereby stepped up to the concentration of the solution last-mixed with the starting material before the former solution contacted the mass of starting material. It is in this way that the concentration values for the separate amounts of extract solution are increased step by step in the vessels 3 until the desired concentration gradient has been produced in the solutions.

Once the concentration gradient has been produced, the extraction process of the present invention can be undertaken continuously, with the only requirement that the extracted lupin seed be replaced after each cycle. In this regard, it should be remembered that at the end of each cycle the extracting of the lupin seed is effected with pure water, so that the lupin seed is debittered as completely as possible and the bitter substances (and substances occurring therewith) from the lupin seed are optionally concentrated in the extract solutions.

For full extraction of the lupin seeds, it is important to keep to certain values for the heights of the layers of extraction mass and of the filter cake produced by pumping off the extract solution in the extractor. At the start of every extracting operation, the mass of starting material on the filter in the extractor is preferably in a layer of 5 to 50 mm, more particularly 10 to 25 mm, in height. The filter cake (while still wet) produced in the extraction apparatus at the end of every extracting operation is preferably a layer with a height in a range of a few millimeters to 30 millimeters at most, and more preferably in the range of 5 to 15 mm. Such a height for the wet filter cake is equal to a height of dry filter cake of 2.5 to 6 mm, or a weight of 2 to 5 kg/m2.

At the end of the extracting operation, there is preferably a drying operation for drying the filter cake and freeing it from the remaining water. The drying of the filter cake can be accomplished by heating and driving out the water, in the form of steam, or by expressing the water. In any event, a useful effect is produced if the amount of water still present in the filter cake at the end of extracting operation is as low as possible. To make certain that this is so, the degree of vacuum used for drawing off the extractant liquid can be increased in steps. By continuously smoothing over the cracks formed in the filter cake when drawing off liquid, it is possible to get a filter cake containing only 40 to 50% water at the end of the extraction operation, i.e., the amount of water to be extracted from the filter cake on drying is roughly equal to the weight of dry matter.

The drying of the filter cake can occur in the extractor itself by supplying heat artificial to the extractor; alternatively, the filter cake can be dried in the sun. The filter cake can also be dried outside the extractor using artificial or natural heat, or the remaining liquid in the filter cake can be expressed, as noted above. The resulting dried, debittered lupin seed product is a high quality foodstuff and animal feed, in which the level of the bitter substances still present has been decreased to 0.002%, while the levels of protein and fat are generally the same as in the lupin seed before debittering.

The lupin seed extract with the bitter substances has a level of dry matter equal to 10 to 30%, more preferably 20 to 25%, and also contains carbohydrates, fats, proteins and small amounts of minerals in addition to the water-soluble alkaloids. The extract is dried after an optional concentration step. For drying, the extract is placed in a current of dehumidified air or in an inert gas current at a low temperature, e.g., under 30° C., while it is supported on a support that lets the air through, in the drying housings 4 of the drying apparatus.

The dry product produced in this way is a high-value material with many uses, more specially in agriculture and forestry. When used in the form of a dilute solution in water, for example, in a concentration of 0.2 to 5% based on dry matter, or in the form of a powder, it is responsible for greatly increasing the rate of growth and the size of the plants. Depending on the crop, the yields may be increased by 5 to 30% by using the lupin seed extract, where "yield" is expressed as crop weight per unit area of cultivated field.

Figure 2:
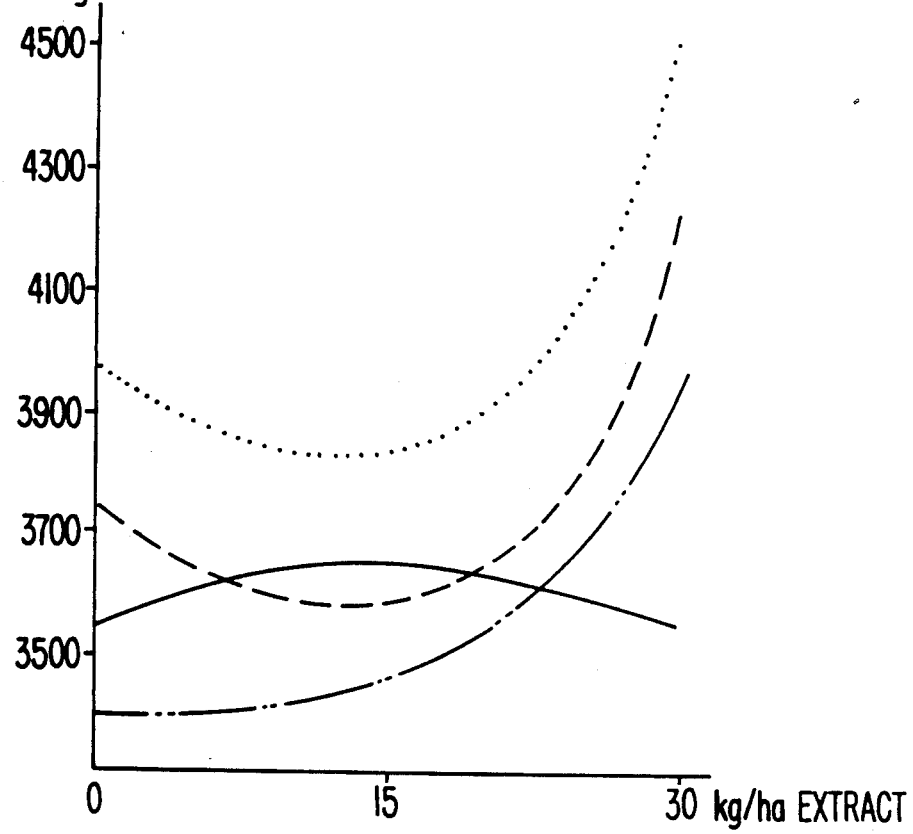
FIGS. 2 through 4 are each graphs showing the effect on yield of applying a composition of the present invention to potato, winter wheat and three different vegetable crops, respectively.
Figure 3:
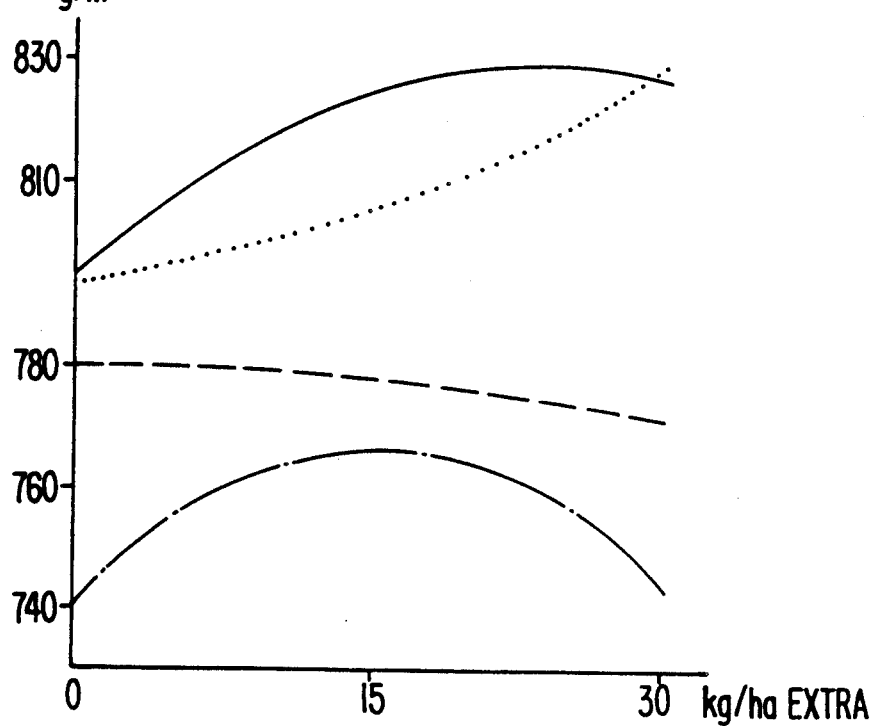
Figure 4:
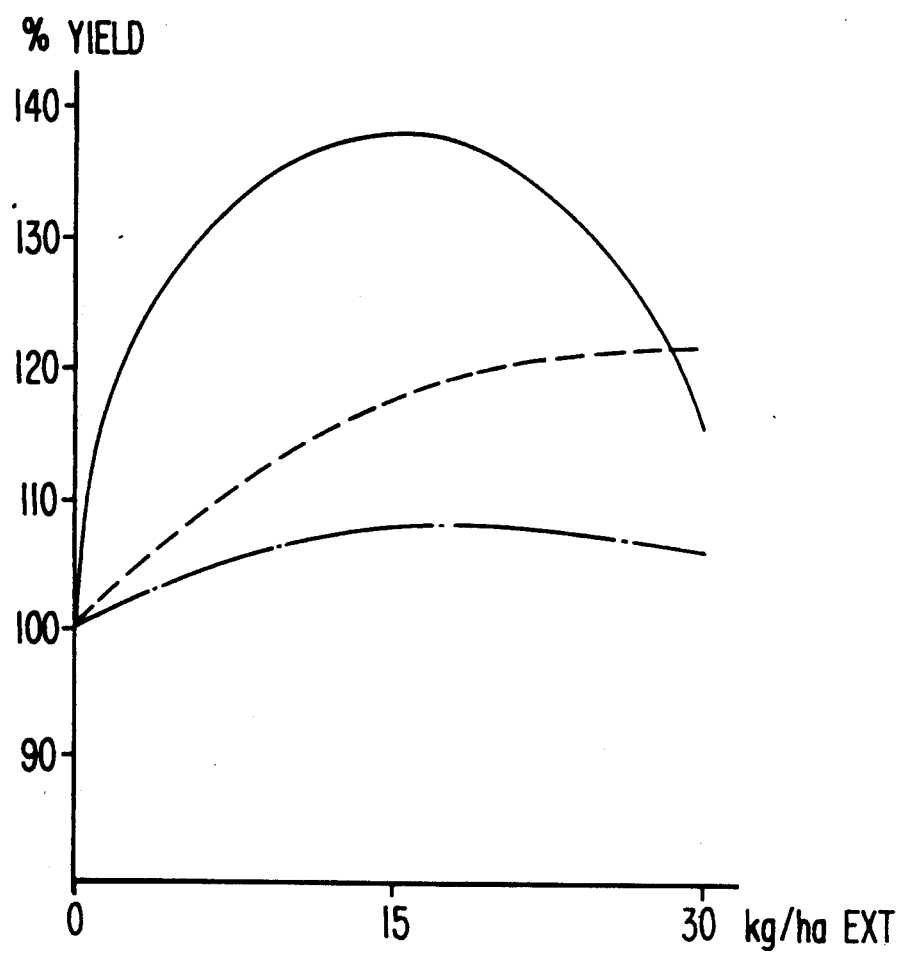

For example, bitter substance-containing material (approximate nitrogen content: 10%; alkaloids: 5%) prepared from lupin seed in accordance with the present invention was dissolved in water and sprayed on potatoes, either when the plants reached a height of 10 to 12 cm or with the onset of tuber formation. An increase in yield of between 14 and 17% was observed when the equivalent of about 30 kilograms per hectare of the lupin-seed material was applied. As shown in FIG. 1, the observed yield-enhancing effect was influenced to some extent by the amount of fertilizer used, as expressed in kilograms of nitrogen equivalent (N) per hectare. Application of an aqueous solution of a bitter substance-containing material derived from lupin seed, in accordance with the present invention, also enhanced the yield of winter wheat (FIG. 2), Chinese cabbage, onion and carrot (FIG. 3). Increased yields were likewise effected by the application of bitter substance-containing material in aqueous solution to soybeans and varieties representing three different species of domestic bitter lupin.

The percentage increase in yield achieved by application of bitter substance-containing material in accordance with the present invention was influenced by the crop involved, the amount of fertilizer used, and/or the mode of application, e.g., by spraying on leaves or by soil application to the roots. In any event, the optimum combination of applied amounts of bitter substance-containing material and fertilizer, and the preferred mode of application, is readily determinable for each crop.

It has also been discovered that pretreating seeds of certain crops with an aqueous solution of a bitter substance-containing material derived from lupin seed, in accordance with the present invention, can increase the percentage of seed germination. As shown in the following table, for example, sets of carrot seeds, with 44 seeds per set, displayed differing percentages of germination in sand when the seeds were pretreated, respectively, by soaking for 24 hours in distilled water (control group) and in aqueous solutions that contained increasing amounts of the bitter substance-containing material.

TABLE 1

Effect of different concentrations of a bitter lupin-derived material on the germination of carrot seeds

| Pretreatment | Number of seedlings (out of 44 possible) |
|---|---|
| Distilled water | 37 |
| 0.01 mg extract/seed | 39 |
| 0.1 mg extract/seed | 37 |
| 0.2 mg extract/seed | 43 |
| 1.0 mg extract/seed | 42 |

When applied at an appropriate rate, which can be readily worked out by simple testing, the lupin seed extract, containing bitter substances in accordance with the present invention, also has a powerful effect against many plant pests.

The debittering process of the present invention can be used for producing oil from lupin seed whatever process, if any, is used before or after extraction. The use of the process of the present invention before another process provides an advantage, however, in that the filter cake produced can be granulated, making the production of oil much simpler.

What is claimed is:

1. A dry composition comprising a material which contains bitter substances extractable from bitter lupin seed, said material being a product of a process comprising the steps of:
   (a) providing a series of separate extract solutions, each solution of said series having a differing concentration of said bitter substances, said series having at least a highest-, a second highest-, and a lowest-concentration extract solution;
   (b) providing a filter medium comprised of a layer of particulate material comprised of bitter lupin seed, which filter medium is contacted by said highest-concentration extract solution in said series;
   (c) sequentially contacting said layer with each extract solution of the remaining extract solutions in said series, respectively, in a predetermined order of decreasing concentration of said bitter substances;
   (d) after step (c), contacting said layer with pure water;
   (e) removing said highest-concentration extract solution from said series, so that said second highest-concentration extract becomes the highest-concentration extract solution in said series;
   (f) repeating steps (b) through (e) at least once; and then
   (g) drying at least extract solution from said series at a temperature such that a dry powder is provided which promotes plant growth, wherein (i) said particulate material is comprised of bitter lupin seed which is reduced to a particle size in the range of about 1 to about 50 microns, (ii) said layer of said particulate material is between about 5 and about 50 mm in thickness, (iii) said highest-concentration extract solution contains a percentage of dry mass between about 10 and 30%, and (iv) said steps (b), (c) and (d) are carried out at a temperature of about 30° C. or less.

2. A composition as claimed in claim 1, wherein said bitter lupin seed is reduced to a particle size in the range of about 1 to about 50 microns by milling of said seed before step (b).

3. A composition as claimed in claim 1, wherein said milling comprises ball milling.

4. A composition as claimed in claim 1, wherein step (c) comprises agitating said filter medium such that bitter lupin seed comprising said particulate material is reduced to a particle size in the range of about 1 to about 50 microns.

5. A composition as claimed in claim 4, wherein step (b) comprises coarse milling of said bitter lupin seed to provide particulate material for said filter medium.

6. A composition as claimed in claim 1, wherein said drying is accomplished by placing the said extract solution in a current of dehumidified air or inert gas.

7. A composition as claimed in claim 1, wherein said drying is accomplished at a temperature below 30° C.

8. A method for treating a plant, comprising the step of applying to said plant an amount of the composition claimed in claim 1 which is sufficient to promote the growth of said plant.

9. A method as claimed in claim 8, wherein said plant is selected from the group consisting of potato, winter wheat, Chinese cabbage, onion, carrot, soybean and bitter lupin.

10. A method as claimed in claim 8, wherein said composition comprises a physiologically compatible carrier in which said material containing bitter substances is soluble.

11. A method as claimed in claim 10, wherein said carrier is water.

12. A method as claimed in claim 11, wherein said composition is sprayed on leaves of said plant.

13. A method as claimed in claim 11, wherein said composition is applied to roots of said plant.

14. A method as claimed in claim 8, wherein the yield of said plant is promoted by the application of said composition.

15. A method as claimed in claim 8, wherein said bitter lupin seed is reduced to a particle size in the range of about 1 to about 50 microns by milling of said seed before step (b).

16. A method as claimed in claim 15, wherein said milling comprises ball milling.

17. A method as claimed in claim 8, wherein step (c) comprises agitating said filter medium such that bitter lupin seed comprising said particulate material is reduced to a particle size in the range of about 1 to about 50 microns.

18. A method as claimed in claim 17, wherein step (b) comprises coarse milling of said bitter lupin seed to provide particulate material for said filter medium.

* * * * *